United States Patent [19]

Cambier et al.

[11] Patent Number: 5,202,932
[45] Date of Patent: Apr. 13, 1993

[54] X-RAY GENERATING APPARATUS AND ASSOCIATED METHOD

[75] Inventors: James L. Cambier, Rome; David Pasiak, Waterville, both of N.Y.

[73] Assignee: Catawa Pty. Ltd., Australia

[21] Appl. No.: 750,450

[22] Filed: Aug. 20, 1991

Related U.S. Application Data

[63] Continuation of Ser. No. 535,179, Jun. 8, 1990, abandoned.

[51] Int. Cl.⁵ ............................................. G06K 9/36
[52] U.S. Cl. ...................................... 382/8; 356/237; 358/106; 378/57
[58] Field of Search ............. 378/95, 57, 58, 101–107; 382/8, 47, 34, 56; 358/106; 356/237

[56] References Cited

U.S. PATENT DOCUMENTS

| | | |
|---|---|---|
| 2,879,404 | 3/1959 | Rogers et al. |
| 3,103,591 | 9/1963 | Rogers et al. |
| 3,109,093 | 10/1963 | Arrison, Jr. et al. |
| 3,171,030 | 2/1965 | Foster et al. |
| 3,294,973 | 12/1966 | Jacobs |
| 3,919,467 | 11/1975 | Peugeot |
| 3,958,078 | 5/1976 | Fowler et al. |
| 4,051,378 | 9/1977 | Krippner |
| 4,212,397 | 7/1980 | Bockelmann |
| 4,415,980 | 11/1983 | Buchanan |
| 4,430,568 | 2/1984 | Yoshida et al. |
| 4,614,999 | 9/1986 | Onodera et al. |
| 4,758,782 | 7/1988 | Kobayashi .................. 382/8 |
| 4,771,470 | 9/1988 | Geiser et al. ................ 382/54 |
| 4,783,795 | 11/1988 | Yahata |
| 4,809,308 | 2/1989 | Adams et al. ................ 382/8 |
| 4,852,131 | 7/1989 | Armistead .................... 382/8 |
| 4,879,734 | 11/1989 | Schreckendgust ........ 378/57 |
| 4,893,346 | 1/1990 | Bishop ............................. 382/8 |
| 5,046,120 | 9/1991 | Bishop ............................. 382/8 |

FOREIGN PATENT DOCUMENTS

0096440 12/1983 European Pat. Off.
0138486 4/1985 European Pat. Off.

Primary Examiner—David K. Moore
Assistant Examiner—David Fox
Attorney, Agent, or Firm—Larson and Taylor

[57] ABSTRACT

An X-ray generator and associated method are disclosed. The X-ray generator and method are provided for inspection of objects which are conveyed into an inspection station which includes an X-ray device and image processing device. The X-ray device directs high-energy, short-pulse X-rays toward an object as the object moves into a desired position. This X-ray radiation is received by a video camera and the resulting image is then digitized and transmitted to an image processing device which analyzes the information and determines whether or not the object conforms to a predetermined standard threshold. One aspect of the apparatus includes a rejection device which will remove objects which do not pass inspection thresholds.

16 Claims, 4 Drawing Sheets

X-RAY GENERATING APPARATUS AND ASSOCIATED METHOD

This is a continuation of application Ser. No. 07/535,179, filed Jun. 8, 1990, now abandoned.

BACKGROUND OF THE INVENTION

1. Field of the Invention

This invention relates to an x-ray generating apparatus which produces precise, short pulses of X-ray energy and can do so asynchronously. The X ray generating apparatus and associated method are also disclosed with respect to inspection of objects such as containers for products. An inspection is carried out utilizing computer image processing techniques to analyze an image produced using the X-ray pulses in order to detect foreign materials, defects and the like in the container, or to check for missing components.

2. Description of the Prior Art

A critical step in the manufacturing of any type of consumer product, especially in the area of processed foods and medicines, is the inspection of containers to determine if there are defects, foreign materials or any undesired object present in any container. Foreign materials, such as broken glass or metal chips, if contained in processed foods are a serious threat to consumer health and safety. Thus, it is desirable that essentially every container that is manufactured and/or processed in a plant be inspected before leaving the plant. However, when a large number of containers are manufactured, it can be extremely time consuming and expensive to subject each container to a rigorous inspection.

One known technique of inspecting containers for defects involves sampling. This involves statistical techniques for estimating the presence or absence of foreign materials in packages by inspecting a statistically determined number of containers. Of course, this technique is not perfect as it is limited by the sampling nature of the technique, and inevitably some containers with defects will leave the plant and may eventually reach the consumer.

Alternatively, if equipment failure which could result in contamination is discovered at a manufacturing plant, all production is stopped and items generated subsequent to the last time the equipment was checked are quarantined. The items are then either destroyed or, in some cases, they are x-rayed and individually inspected to check for contaminants. This procedure can result in production delays and lost inventory.

Although it has been known to provide X-ray inspection of containers, the inspection of fast moving objects requires X-ray pulses of very short duration. It is known to provide precisely timed ultra-short X-ray pulses for various purposes. See U.S. Pat. Nos. 2,879,404 and 3,103,591. These patents are primarily concerned with medical uses of X-ray technology, i.e., angiography, where it is desired to not only get high resolution pictures of moving blood vessels but also to limit patient dosages of X-rays.

It is also known to provide high voltage X-ray pulses in synchronization with a camera shutter, an AC cycle, or a pulse generator in the primary circuit of a transformer See U.S. Pat. Nos. 3,109,093, 3,294,973 and 4,614,999. These devices are not particularly useful when it is desired to generate pulses asynchronously in response to external events, such as the arrival of containers at an inspection point.

Despite these prior art methods and devices, there remains a need for an efficient cost effective way to inspect every container on a high speed assembly line. There also remains a need for an X-ray pulse generator that is triggered by the arrival of the container to be inspected at the inspection position.

SUMMARY OF THE INVENTION

The present invention involves an inspection apparatus and an X-ray generating apparatus which generates high-energy, short-pulse X-rays. The X-ray generator is disclosed as used in the context of an inspection apparatus, however, it has other applications as well. The inspection apparatus including the X-ray generating assembly are placed on-line after containers have been fully processed and filled with the intended contents and sealed. The inspection in accordance with the present invention is preferably carried out prior to packaging of the sealed containers for shipping. The containers are conveyed into an inspection station which includes an X-ray device and an image processing device. The X-ray device directs high-energy short pulsed X-rays toward the container as the container moves through the inspection station. The X-rays impinge upon the container, and a sensor receives an image which is received by a video camera. The video camera sends its signal to the image processing device of the present invention which generates digital image information representative of the container. This information is then compared with stored standard image information. In the comparison step, a measurement is taken of the actual image and this is compared to a predetermined standard image measurement. It is then determined whether or not the container conforms to the standard. If a non-conformity with the predetermined standard is detected, a reject signal is generated by associated signal-generating circuitry.

The system includes a rejection means such as a suction cup starwheel to remove the contaminated container from the conveyor line when a reject signal is transmitted. The rejected containers may be collected in a bin or conveyed to a remote location as desired.

It is an object of the invention to provide an X-ray generating apparatus for producing high-energy, short-pulse X-rays in response to an asynchronous signal.

It is an object of the invention to provide an apparatus which is capable of rapidly inspecting every container coming off a processing line for defects, contaminants or the like.

It is a further object of the invention to provide an inspection apparatus that can be used to detect small contaminants such as glass chips, metal fragments and stones inside filled and sealed containers.

It is a further object of the invention to provide an inspection apparatus that can be used to inspect different products and container sizes.

It is a further object of the invention to provide asynchronous short-pulse high-energy X-rays to capture high quality images of containers moving at line speeds.

It is a further object of the invention to provide for operation of the inspection device at container rates of up to about 1200 per minute and line speeds of up to about 180 feet per minute.

It is a further object of the invention to provide an operation having sensitivity to glass fragments as small as about 0.050 inches long and metal fragments as small as about 0.020 inches long.

It is a further object of the invention to provide a system that detects defects, missing parts and non-glass contaminants in a container, and then removes such containers from the line.

It is a further object of the invention to provide an image processing method and apparatus that is adaptable for use with different inspection procedures and which system is not thwarted by ornamental designs on the sidewalls. In addition, the system can be adapted to accommodate elements such as metal tab tops and irregularly shaped packages.

It is a further object of the invention to provide a system which can utilize certain existing X-ray concepts.

These and other objects of the invention will be fully understood from the following description of the invention with reference to the drawings appended to this Application.

DESCRIPTION OF THE PREFERRED EMBODIMENTS

Figure 1:
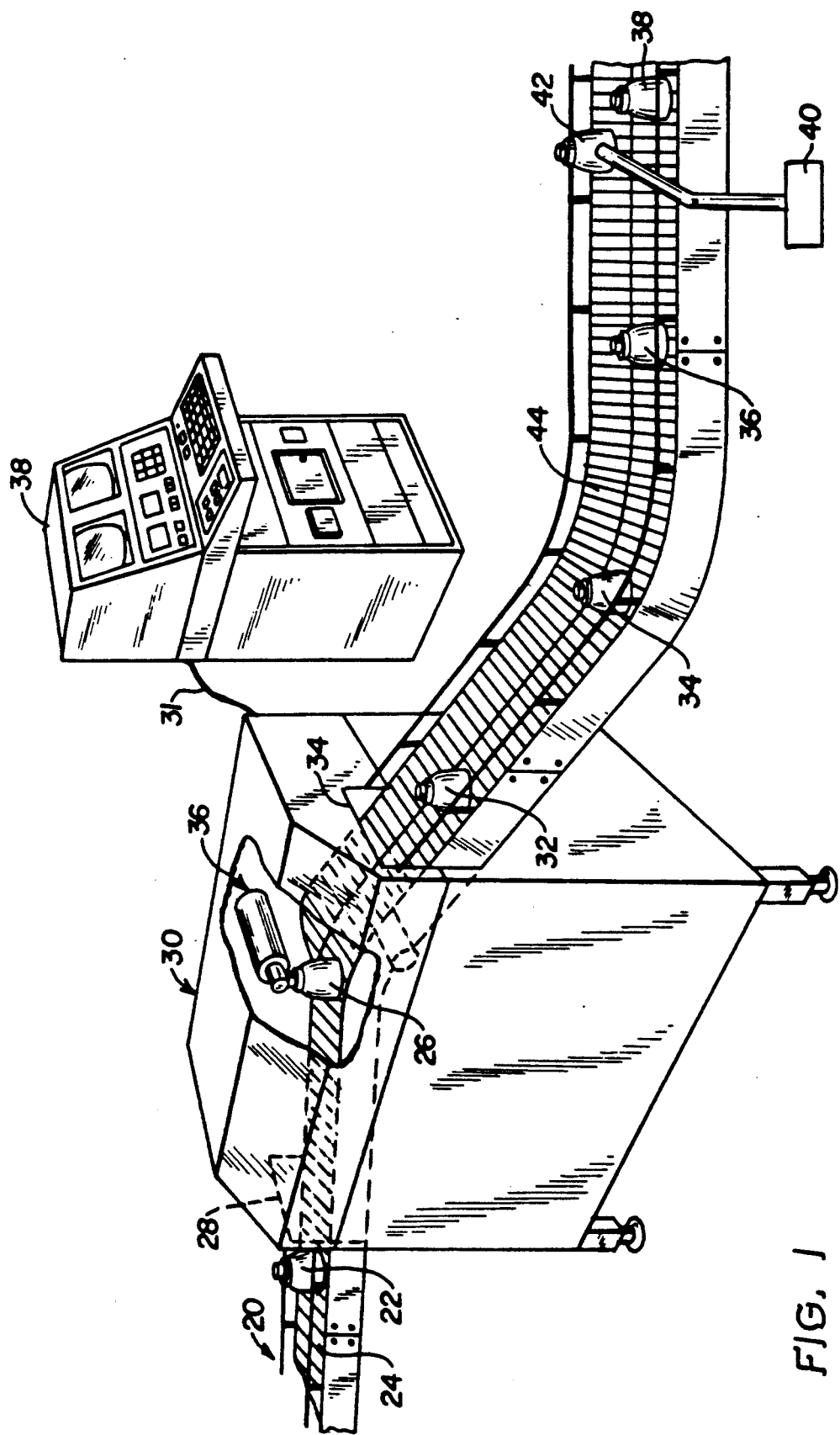
FIG. 1 is a schematic elevation of an inspection system in accordance with the present invention.

Referring to FIG. 1, the inspection apparatus and associated X-ray generating apparatus are discussed in the context of a standard conveyor product line 20. It should be understood, however, that the present invention could be successfully employed in a variety of applications. Line 20 conveys incoming processed product containers 22 on conveyor belt 24 from another part of the assembly plant (not shown) to a point where the product containers such as container 22 will be packed for shipping. A standard conveyor typically operates at a rate of about 50 to 200 feet per minute. A filled sealed container 26 enters into one end 28 of an inspection station 30. After an inspection in accordance with the present invention as discussed more fully below, outgoing containers such as containers 32 exit through the opposite end 34 of station 30. Inspection station 30 contains X-ray generator 36 which directs an X-ray pulse at the container 26 when it arrives at the appropriate point of the inspection station 30.

An X-ray pulse is directed toward and impinged upon container 26 and the X-ray radiation is converted into an image and processed by circuitry in the following manner. A portion of the X-ray pulse generated by X-ray generator 36 passes through container 32. An image is generated and processed as discussed hereinafter. The processed image is compared, in the manner described herein, in control panel 38, which is connected to inspection station 30 as schematically depicted by connection lead 31. If an incoming container 26 does not conform to a predetermined standard a reject signal is emitted and an operator of control panel 38 can initiate a reject procedure of a type which would be readily understood by those skilled in the art. Alternatively, a reject device 40 may be provided to automatically remove rejected containers from the line. Preferably, reject device 40 is a pneumatically driven plunger assembly. Under such circumstances, device 40 pushes a rejected container 42 onto an alternative belt 44 from which the rejected container 42 may be collected and eliminated from the inventory to be packaged Accepted containers 34, 36 and 38 continue on conveyor belt 24 to the packaging area (not shown). The system is capable of operating with conveyor belts which operate at typical container rates of up to about 1200 per minute.

Figure 2:
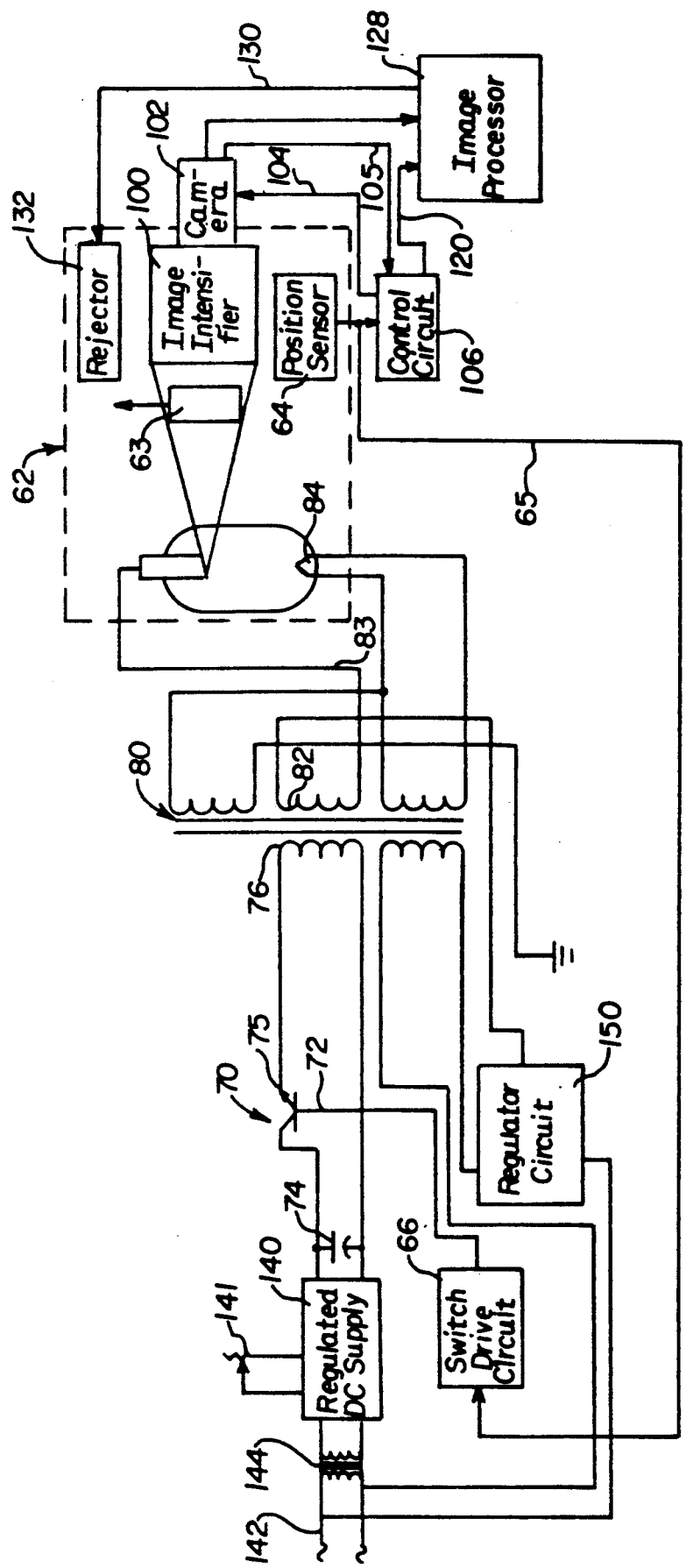
FIG. 2 is a combined circuit and block diagram of one embodiment of suitable circuitry for the inspection system of the present invention.

Referring to FIG. 2, the inspection area is generally designated by dashed box 62. A position sensor 64, which is preferably a photosensor or a magnetic proximity switch generates a signal when the container 63 is optimally positioned. When the container 63 is optimally positioned, an X-ray pulse is directed toward it and impinged upon the container 63. When there is no container in position, then no X-ray pulse is produced by the system of the present invention. The position sensor signal is transmitted by line 65 to a switch drive circuit 66. Switch drive circuit 66 is preferably an SN 74LS74 flip-flop and an SN 74LS393 counter which, as would be understood by those skilled in the art, produce a precisely timed TTL (transistor-transistor logic) pulse which in turn controls the switch drive circuit 66. Switch drive circuit 66 activates a high voltage switching transistor 70 at base 72. When high voltage switch 70 is activated, this allows charge stored in capacitor 74 to discharge. The current flowing into base 72 causes a much larger current to flow at collector 75. The charge packet is delivered to primary winding 76 of high voltage transformer 80. This causes a high voltage pulse to be generated in the secondary 82 of the transformer 80. As used herein, a "high voltage" pulse is a pulse of between about 40 to 70 kilovolts. The pulse is applied by lead 83 to X-ray tube 84 to generate an X-ray pulse. The polarities of the transformer windings and of the current pulses may be arranged so that only voltage pulses of the correct polarity are applied to the tube 84 as appropriate to the particular circumstances in which the system is used. The pulses generated are of a short duration of between about 0.5 to 5.0 milliseconds, and preferably the pulses are of a duration between about 1.0 and 2.0 milliseconds.

The X-ray energy transmitted through the container 63 is detected by an image intensifier tube 100 and converted visible light image Which is sense by a video camera to a 102. A suitable camera 102 would be one which employs CID (charge injection device) technology. An example of a suitable camera is a CIDTEC Model 2505A2. As discussed hereinafter, the video image is then sent to image processor 128 which is a computer suitably programmed to digitize the signal and extract certain measurements which are compared to stored standard image measurements. If the measurement values are not within a range dictated by the stored standards, a rejection signal is generated by the image processor 128 and transferred by line 130 to a rejector 132 which removes container 63 from the line.

Camera 102 is gated through line 104 by control circuit 106. The gate signal transmitted by control circuit 106 inhibits readout of the stored charge pattern corresponding to an image. This inhibition is desirable because the readout process destroys the stored charge pattern (and thereby the image). As a result, it is preferred to inhibit the readout until the external image digitization device of image processor 128 is ready to store it in digital form.

In addition, as would be understood by those skilled in the art, image capture can begin only at the beginning of a video field, that is, immediately after the vertical retrace interval. For asynchronous image application as desired for purposes of the present invention, the gate signal is generated simultaneously with the X-ray pulse which is controlled by switch drive circuit 66. The gate signal continues until the beginning of the next vertical retrace pulse. This prevents loss of image data should the X-ray pulse occur in the middle of a video field. In addition, it allows the X-ray imaging pulse to be generated asynchronously and independent of the timing of the video signals. Camera 102 sends timing information through a sync line 105 in the form of the vertical retrace pulse as mentioned hereinbefore to control circuit 106. Control circuit 106 utilizes this information for the timing of the initiation and termination of the gate pulse. The timing information is also used by control circuit 106 to issue a trigger pulse to image processor 128 to trigger it to digitize the image.

The gate pulse is returned to its normal state at the beginning of a video field as stated hereinbefore. The two next following video fields contain the image information associated with the container 63 to be inspected. At the time the gate pulse returns to its normal state, a trigger signal is simultaneously transmitted across line 120 from control circuit 106 to image processor 128. This signal commands image processor 128 to digitize the next full field or frame, depending on the application of video information.

Image processor 128 performs the digitization function and thereafter performs a comparison function to compare the image of container 63 with the stored standard. The method of performing the comparison step is discussed more fully hereinbelow.

If a decision is made to reject the package, a reject signal is generated and transmitted by line 130 to the rejector 132. Depending on the type of container or item being inspected, rejector 132 may be a short duration jet of compressed air, a pneumatically actuated cylinder, or another electromechanical device. The preferred device for small glass containers is a vacuum starwheel as manufactured by Industrial Dynamics, Torrance, California or Peco Controls of Milpitas, California.

Turning more specifically to regulation of the X-ray pulses, control of the high voltage is accomplished by using a highly regulated DC power supply 140 which is preferably adjustable as indicated by reference character 141.

The regulated DC power supply 140 preferably consists of a full wave bridge rectifier using 80 VAC input, followed by a Motorola MC1466 monolithic voltage and current regulator manufactured by Motorola Corporation of Schaumburg, Illinois. This is a single integrated circuit which controls an external series pass transistor which is preferably a Motorola MJ413. The supply delivers about 0 to 80 volts DC at maximum current of about 0.5 amps.

Power to the DC supply 140 is provided by a standard AC line 142 which is rectified within DC supply 140 as indicated hereinbefore.

DC supply 140 allows capacitor 74 to be recharged to a fixed voltage level between pulses, so that the high voltage pulses generated in the secondary 82 of the transformer 80 will have constant amplitude which means that the X-ray pulses generated are of a substantially constant magnitude.

Current flowing into X-ray tube 84 is preferably regulated by regulator circuit 150. Regulator circuit 150 measures the current which flows through the X-ray tube 84 with each pulse by integrating the total current during the duration of the pulse. The integrated current is applied to a feedback control system which compares it to a reference current set by an adjust control which is included in regulator circuit 150. Any error which may be detected is corrected and the filament current of the X-ray tube 84 is thereby controlled.

Figure 3:
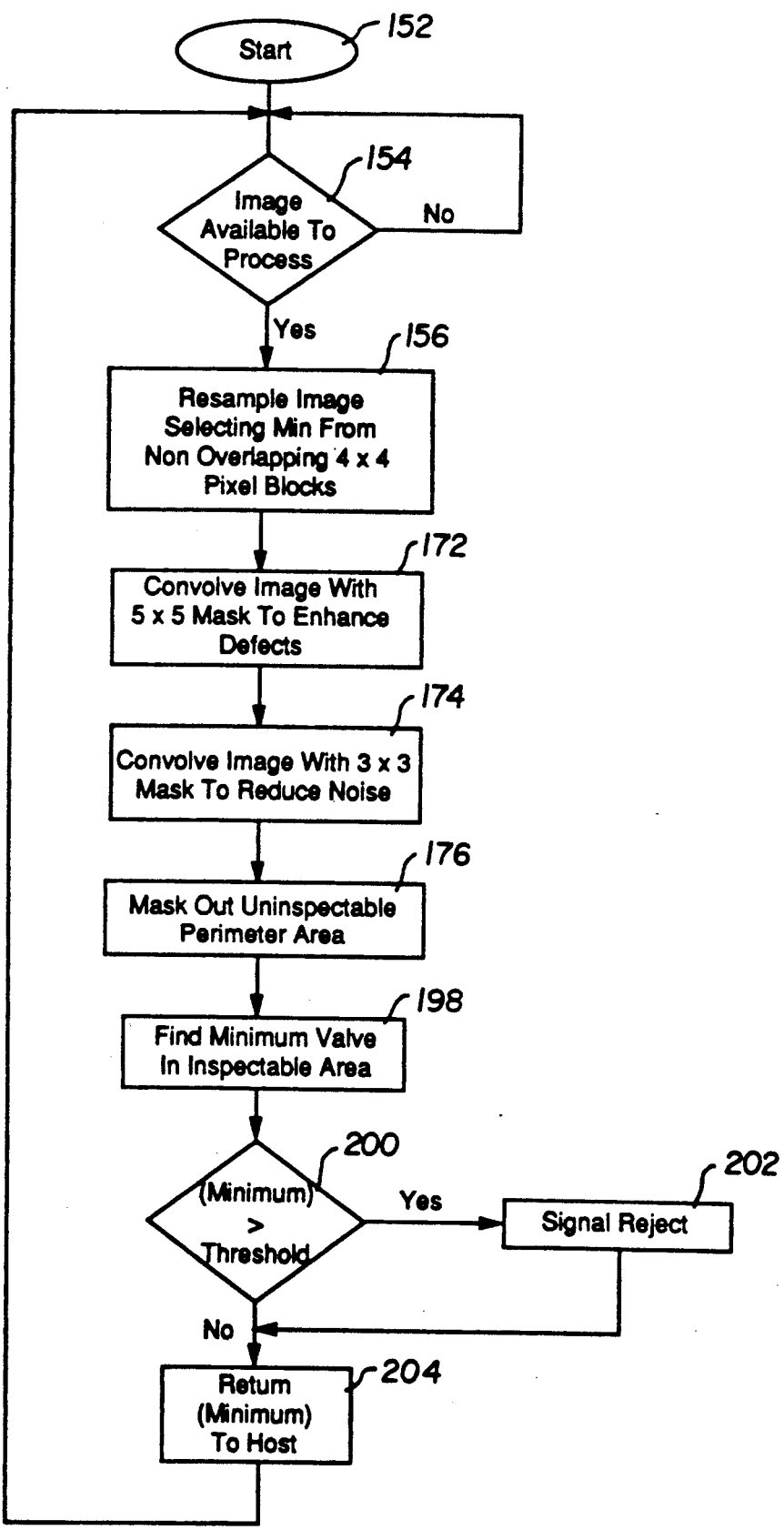
FIG. 3 is a flow chart of the image processing software of the present invention.

Referring now to FIG. 3, the computer software used in image processor 128 of FIG. 2 is described with reference to the flow chart (shown in FIG. 3). A start function is initiated as depicted by reference character 152. Query 154 determines whether there is an image available to process. If the answer is no, the program returns to start 152. If the answer is yes, the program proceeds to step 154 where the image is resampled. A minimum image is created using preferably non-overlapping 4×4 pixel blocks.

Figure 4:
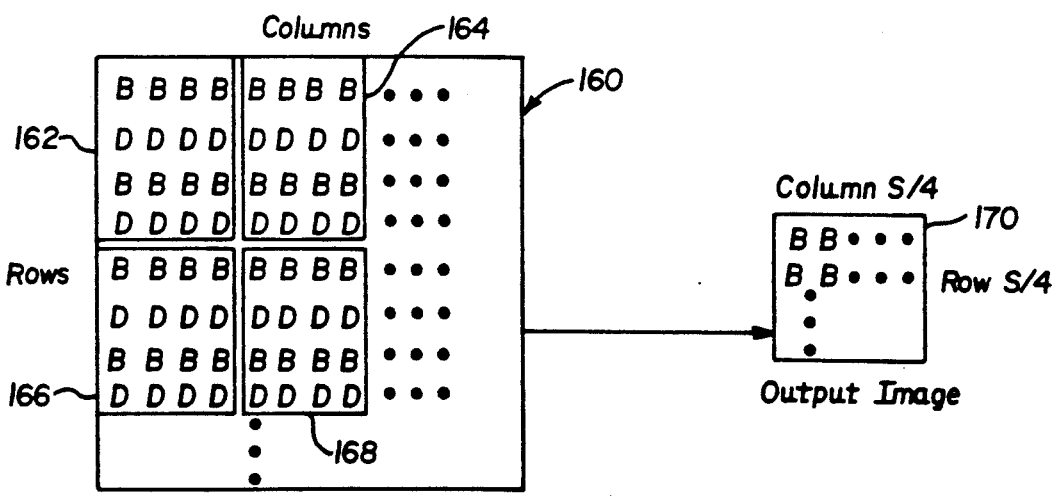
FIG. 4 is a schematic diagram of the pixel blocks used to construct the output image for the present invention.

More specifically, as shown in FIG. 4, the original digitized input image is shown schematically as large block 160. Image 160 is divided into 4×4 pixel blocks and several exemplary 4×4 blocks are depicted as shown by reference characters 162, 164, 166 and 168. Input image 160 is made up of approximately 10,000 of such 4×4 blocks. The minimum pixel from the bright video field of each 4×4 pixel block in the input image 160 is selected and used to construct the resampled output image 170. The bright video field designated "B" in FIG. 4 is determined by comparing the pixel summations of odd- versus even-numbered rows from a 4×4 pixel block in the middle of the input image 160.

Referring again to the flowchart of FIG. 3, after the image is resampled as discussed with reference to FIG. 4, the method of the present invention includes step 172 in which the resampled image 170 is convolved with, preferably, a 5×5 mask to enhance defects. The enhance mask would preferably take the following form:

$$\begin{bmatrix} -0.04 & -0.04 & -0.04 & -0.04 & -0.04 \\ -0.04 & -1.04 & -1.04 & -1.04 & -0.04 \\ -0.04 & -1.04 & 8.96 & -1.04 & -0.04 \\ -0.04 & -1.04 & -1.04 & -1.04 & -0.04 \\ -0.04 & -0.04 & -0.04 & -0.04 & -0.04 \end{bmatrix}$$

Thereafter, the image 170 which has been enhanced with the 5×5 mask is now convolved with preferably a 3×3 mask to reduce noise, and this step is depicted at block 174 of the flowchart. (FIG. 3) The noise mask is preferably of the following form:

$$\begin{bmatrix} 0.0 & 0.2 & 0.0 \\ 0.2 & 0.2 & 0.2 \\ 0.0 & 0.2 & 0.0 \end{bmatrix}$$

After noise reduction step 174, the method provides for masking out the uninspectable perimeter area as designated by reference character 176.

Figure 5A:
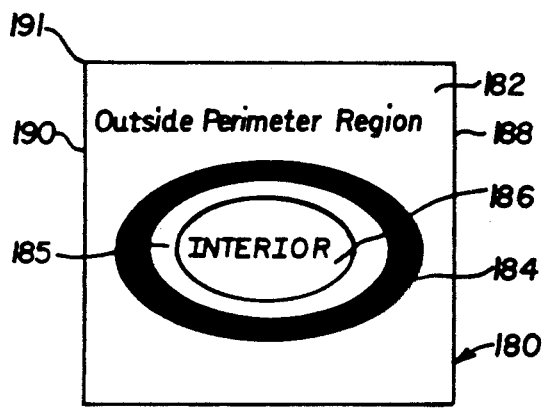
FIG. 5A is a schematic illustration of an exemplary input image generated by the image processing device of the present invention.
Figure 5B:
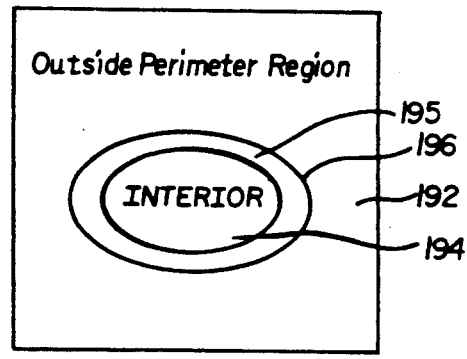
FIG. 5B is a schematic illustration of an exemplary output image generated by the image processing device of the present invention.

This step is best understood with reference to FIGS. 5A and 5B. In FIG. 5A, the input image is designated by reference character 180. Outside perimeter region 182 is the area outside the image and would be grey in intensity. Dark elliptical boundary area 184 represents the boundary of the inspectable area as discussed hereinafter. Dark elliptical boundary area 184 and brighter elliptical area 185 are the result of the 5×5 enhance mask operation. The ellipse where boundary area 184 meets 185 represents the edge of the inspectable interior composed of regions 185 and 186. Brighter elliptical area 185 is brighter than both outside perimeter region 182 and interior 186. The interior 186 is of about the same intensity as outside perimeter region 182. A container would be moving across the field from left to right and the leading edge of the image is designated by reference character 188. The opposite edge is designated by reference character 190.

Referring still to FIGS. 5A and 5B, the method of the present invention includes starting analysis at the leading edge 188 of input image 180 and gradually moving towards the center. As this is done by processor 128, all or substantially all pixels along any given row are preferably masked out. That i s, the masked out pixels are assigned a certain intensity from the outside perimeter area 182. This is done until the edge of the boundary area 184 is detected. Specifically, along any given row, the edge of area 184 is denoted by pixel intensity change from grey to black. When this change from grey to black is detected, the outside edge of area 184 is being detected. These pixels are masked out until the edge of area 185 is detected by a pixel intensity change of black to brighter grey. The pixel intensity in the upper left-hand corner 191 in the input image 180 is used to define the transition thresholds for the three regions as follows:

Grey to Black = first pixel intensity − CONSTANT

Black to Brighter Grey = first pixel intensity + CONSTANT

Comparing FIG. 5A to 5B, the results of this function are shown. Outside perimeter region 192 of FIG. 5B is typically of about the same intensity as interior 194. Brighter elliptical area 195 is the result of the enhance mask and it is still visible in FIG. 5B. The edge 196 corresponds to the boundary between areas 184 and 185 of FIG. 5A. In this way, the portions of the image which do not require inspection are masked out, and the inspection is conducted in the inspectable region composed of interior 194 and area 195.

Referring back to FIG. 3, the uninspectable perimeter has now been masked out as indicated by step 176 of the flow chart. A minimum pixel intensity is found in the inspectable region composed of interior 194 and area 195 (FIG. 5B), as designated by block 198 of the flowchart.

The absolute value of this minimum pixel intensity is compared to a standard threshold value, as depicted by reference character 200 (FIG. 3). This is performed once for the entire image. If the actual minimum is outside of a predetermined threshold value, then the program commands that a reject signal be generated as depicted by reference character 202. If the minimum does not exceed the threshold then the program returns to start 152 and the container being inspected is not rejected. The predetermined threshold is determined by processing a large number of known acceptable containers, and analyzing the results using a statistical analysis as would be understood by those skilled in the art. It is preferred to construct a histogram of such minimum values and to determine the threshold from the histogram. The threshold is set so that only a small percentage of about less than 1.0 percent of the containers have a minimum intensity below the threshold. Using this method, glass fragments as small as about 0.050 inches long can be detected and metal fragments as small as about 0.020 inches long can be detected.

In accordance with the method of the present invention, containers which are to be inspected are placed on a conventional product container line 20 (FIG. 1). The inspection of each container includes generating high energy short pulse X-rays towards each container as it arrives at the inspection point. Thereafter, an X-ray image representative of the container then being inspected is generated and a digital signal based on said X-ray image is then produced. The method further includes analyzing the digital signal on a pixel-by-pixel basis including comparison of it to a threshold standard. An accept or reject decision is made based on whether the actual signal is below the threshold and a decision command is generated based upon the analysis.

It should be appreciated that the present invention provides a method and apparatus for generating short-duration X-ray pulses suitable for X-ray imaging of fast-moving objects. The invention provides a low-cost pulsed X-ray source which uses standard X-ray components, yet can generate short-duration pulses in response to an asynchronous external trigger signal, while maintaining excellent voltage and current stability.

Although the invention has been described with reference to the inspection of containers, it should be understood that the X-ray pulse generator is useful in other applications such as inspection of materials for missing or misplaced parts, detection of defects in empty containers, or detection of contaminants in bulk (unpackaged) materials which may be passing by on a conveyor belt.

Whereas particular embodiments of the invention have been described hereinabove, for purposes of illustration, it will be evident to those skilled in the art that numerous variations of the details may be made without departing from the invention as defined in the appended claims.

I claim:

1. A method of inspecting an object comprising the steps of generating an external signal in response to said object being in a predetermined optimal position;

generating a high energy short x-ray pulse in response to said external signal and causing said x-ray pulse to impinge upon said object to provide information for creating an x-ray image of said object;

converting x-ray radiation passing through said object into a visible light image;

converting said visible light image into digital image information;

resampling said digital image information by selecting minimum pixel intensity values from a plurality of pixel portions of said digital image signal;

analyzing said digital image information using a pixel-by-pixel comparison of said signal to a predetermined condition and determining whether a departure from said condition has occurred analyzing said digital image information using the steps of selecting said minimum pixel intensity values from a plurality of pixel blocks of said digital image information;

using said selected minimum pixel intensity values to represent said digital image information in said resampled output image;

convolving said resampled output image with a first mask to enhance irregularities;

convolving said resampled and enhanced output image with a second mask to reduced noise;

searching said resampled and enhanced output image to find an overall minimum pixel intensity value;

comparing said overall minimum pixel intensity value of said resampled output image with a predetermined threshold value; and generating a command signal responsive to said comparison of said overall minimum pixel intensity value with said threshold value.

2. The method of claim 1 including selecting said predetermined threshold value for said overall minimum pixel intensity value by processing a predetermined number of known acceptable objects, and determining a minimum value for each, and performing a statistical analysis of said minimum values, and selecting a predetermined threshold value based upon said statistical analysis.

3. The method of claim 1, including conveying a plurality of objects in sequence and continuously generating and directing said x-ray pulses toward and impinging said pulses upon said objects and effecting said analyzing of said digital image with digital information representative of each said object.

4. The method of claim 3, including generating and directing said X-ray pulses at said objects when said objects are in a position to receive said X-ray pulse.

5. The method of claim 1, including generating said X-ray pulses each having a duration of between about 0.5 and 5.0 milliseconds.

6. The method of claim 1, including selecting as said first mask to enhance irregularities a mask having dimensions of between about 1×1 to 5×5.

7. The method of claim 1, including selecting as said second mask to reduce noise a mask having dimensions of between about 1×1 to 5×5.

8. A method of inspecting an object comprising the steps of generating an external signal in response to said object being in a predetermined optimal position;

generating a high energy short x-ray pulse in response to said external signal and causing said x-ray pulse to impinge upon said object to create an x-ray image of said object;

converting said x-ray image into a digital output image;

convolving said output image with at least one mask;

searching said output image to find an overall minimum pixel intensity value;

comparing said overall minimum pixel intensity value of said output image with a predetermined threshold value and generating a responsive signal when the comparison results in the conclusion that a departure from said predetermined threshold value has been sensed.

9. The method of claim 8 including convolving said output image with a first mask to enhance irregularities; and convolving said enhanced output image with a second mask to reduce electrical noise.

10. The method of claim 8 including selecting minimum pixel intensity values from a plurality of pixel blocks of said digital output image; and using said selected minimum pixel intensity values to represent said digital image information in a resampled output image.

11. The method of claim 8 including selecting said predetermined threshold value for said overall minimum pixel intensity value by processing a predetermined number of known acceptable objects, and determining a minimum value for each, and performing a statistical analysis of said minimum values, and selecting a predetermined threshold value based upon said statistical analysis.

12. The method of claim 10, including conveying a plurality of objects in sequence and continuously generating and directing said x-ray pulses toward and impinging said pulses upon said objects and analyzing digital image information representative of each said object.

13. The method of claim 12, including generating and directing said x-ray pulses at said objects when said objects are in a position to receive said x-ray pulse.

14. The method of claim 8, including generating said x-ray pulses each having a duration of between about 0.5 and 5.0 milliseconds.

15. The method of claim 9, including selecting as said first mask to enhance irregularities a mask having dimensions of between about 1×1 to 5×5.

16. The method of claim 9, including selecting as said second mask to reduce noise a mask having dimensions of between about 1×1 to 5×5.

* * * * *

UNITED STATES PATENT AND TRADEMARK OFFICE
CERTIFICATE OF CORRECTION

PATENT NO. : 5,202,932
DATED : April 13, 1993
INVENTOR(S) : James L. Cambier and David Pasiak It is certified that error appears in the above-indentified patent and that said Letters Patent is hereby corrected as shown below:

Title Page, after Assignee:,"Catawa Pty. Ltd., Australia" should be -- PAR Technology Corp., New Hartford, N.Y. --.

Title Page, under U.S. Patent Documents, change to:
-- 3,958,078  5/1976  Fowler et al. . . . . . 378/57 --.

Column 4, lines 10 and 11, after"packaged", -- . -- should be inserted.

Column 4, line 52, "Which is sense" should be -- which is sensed --.

Column 4, line 53, "to a" should be deleted.

Column 5, line 33, after "128", --This signal commands image processor 128-- should be inserted.

Column 9, line 12, "reduced" should be -- reduce --.

Signed and Sealed this

Twenty-eight Day of February, 1995

Attest:

BRUCE LEHMAN

Attesting Officer       Commissioner of Patents and Trademarks